United States Patent
Schellekens et al.

(10) Patent No.: US 11,744,803 B2
(45) Date of Patent: Sep. 5, 2023

(54) PH-CONTROLLED PULSATILE DELIVERY SYSTEM, METHODS FOR PREPARATION AND USE THEREOF

(75) Inventors: Reinout Cornelus Andreas Schellekens, Groningen (NL); Henderik Willem Frijlink, Eelde (NL)

(73) Assignee: Stichting Groningen Centre for Drug Rese, Groningen (NL)

( * ) Notice: Subject to any disclaimer, the term of this patent is extended or adjusted under 35 U.S.C. 154(b) by 385 days.

(21) Appl. No.: 11/989,112

(22) PCT Filed: Jul. 29, 2005

(86) PCT No.: PCT/NL2005/000559
§ 371 (c)(1),
(2), (4) Date: Mar. 2, 2009

(87) PCT Pub. No.: WO2007/013794
PCT Pub. Date: Feb. 1, 2007

(65) Prior Publication Data
US 2009/0181089 A1  Jul. 16, 2009

(51) Int. Cl.
*A61K 9/48* (2006.01)
*A61K 9/28* (2006.01)
*A61K 31/00* (2006.01)

(52) U.S. Cl.
CPC ............ *A61K 9/4891* (2013.01); *A61K 9/286* (2013.01); *A61K 9/2846* (2013.01); *A61K 9/2866* (2013.01); *A61K 31/00* (2013.01)

(58) Field of Classification Search
CPC .... A61K 9/4891; A61K 9/2846; A61K 9/286; A61K 9/2866; A61K 31/00
See application file for complete search history.

(56) References Cited

U.S. PATENT DOCUMENTS

| | | | |
|---|---|---|---|
| 4,755,385 A * | 7/1988 | Etienne et al. | 424/687 |
| 4,871,549 A | 10/1989 | Ueda et al. | |
| 5,422,121 A | 6/1995 | Lehmann et al. | |
| 6,277,412 B1 | 8/2001 | Otterbeck | |
| 8,911,766 B2 | 12/2014 | Hossainy et al. | |
| 2002/0110593 A1 | 8/2002 | Penhasi et al. | |
| 2003/0049315 A1 | 3/2003 | Daggy et al. | |
| 2003/0011374 A1 | 6/2003 | Percel et al. | |
| 2005/0075432 A1 * | 4/2005 | Verrall | A23L 1/2205 524/284 |
| 2005/0147663 A1 * | 7/2005 | Mohan et al. | 424/451 |
| 2015/0246001 A1 | 9/2015 | Zupancich et al. | |

FOREIGN PATENT DOCUMENTS

| | | |
|---|---|---|
| EP | 0 348 808 A2 | 6/1989 |
| EP | 0384646 B1 | 6/1993 |
| EP | 0 793 959 A1 | 9/1997 |
| EP | 1021171 B1 | 5/2003 |
| GB | 2367002 | 3/2002 |
| JP | 61100526 A | 5/1986 |
| JP | 61118326 A | 6/1986 |
| JP | 62-12717 | 7/1986 |
| JP | H7-196477 | 8/1995 |
| JP | H9-295933 A | 11/1997 |
| JP | 10130171 A | 5/1998 |
| WO | WO 87 05804 A | 10/1987 |
| WO | 98/13029 A1 | 4/1998 |
| WO | 98/43605 A1 | 10/1998 |
| WO | WO 99/61002 | 12/1999 |
| WO | WO 00/03696 | 1/2000 |
| WO | WO 01/66094 A1 | 9/2001 |
| WO | WO 02/17887 A1 | 3/2002 |
| WO | WO 2004/062577 A2 | 7/2004 |
| WO | WO 2007/013794 A1 | 2/2007 |

OTHER PUBLICATIONS

PCT International Search Report, PCT/NL2005/000559, dated Nov. 4, 2005.
PCT International Preliminary Report on Patentability, Application No. PCT/NL2005/000559 dated Jan. 29, 2008.
Khan et al., a pH-dependent colon targeted oral drug delivery system using methacrylic acid copolymers: I. Manipulation of drug release using Eudragit® L100-55 and Eudragit® S100 combinations, Journal of Controlled Release, 1999, pp. 215-22, vol. 58.
Beck et al., Physico-chemical characterization of zein as a film coating polymer, A direct comparison with ethyl cellulose, International Journal of Pharmaceutics, 1996, pp. 137-150, vol. 141, Elsevier Science B.V.
Torres-Giner et al., Stabilization of a Nutraceutical Omega-3 Fatty Acid by Encapsulation in Ultrathin Electrosprayed Zein Prolamine, Journal of Food Science, 2010, N69-N79, vol. 75, Nr. 6, Institute of Food Technologists.
Opposition for European Patent No. 1916995 dated Jul. 29, 2016.
Handbook of Pharmaceutical Excipients, Third Edition, 2000, entry for Polymethacrylates, pp. 401-406, American Pharmaceutical Association, Washington, DC.
Handbook of Pharmaceutical Excipients, Third Edition, 2000, entry for Guar Gum, pp. 232-233, American Pharmaceutical Association, Washington, DC.

(Continued)

*Primary Examiner* — Adam C Milligan
(74) *Attorney, Agent, or Firm* — TraskBritt

(57) ABSTRACT

The invention relates to delivery systems that allow for the pulsatile release of a substance, such as a drug, in response to a change in pH. More specifically, it relates to drug administration to the GI tract, in particular to site-specific intestinal drug delivery via the oral route. Provided is a pH-controlled pulsatile release system (PPRS) comprising a core surrounded by a coating layer, wherein said core comprises an active substance and wherein said coating layer comprises a pH-sensitive coating material wherein a swellable agent is embedded. Said swellable agent is capable of taking up at least 1.1 times, preferably at least 5 times, more preferably at least 10 times its weight in water. Also provided is a pharmaceutical composition comprising a PPRS, in particular a colon-specific PPRS.

20 Claims, 4 Drawing Sheets

(56) References Cited

OTHER PUBLICATIONS

Figure 1:
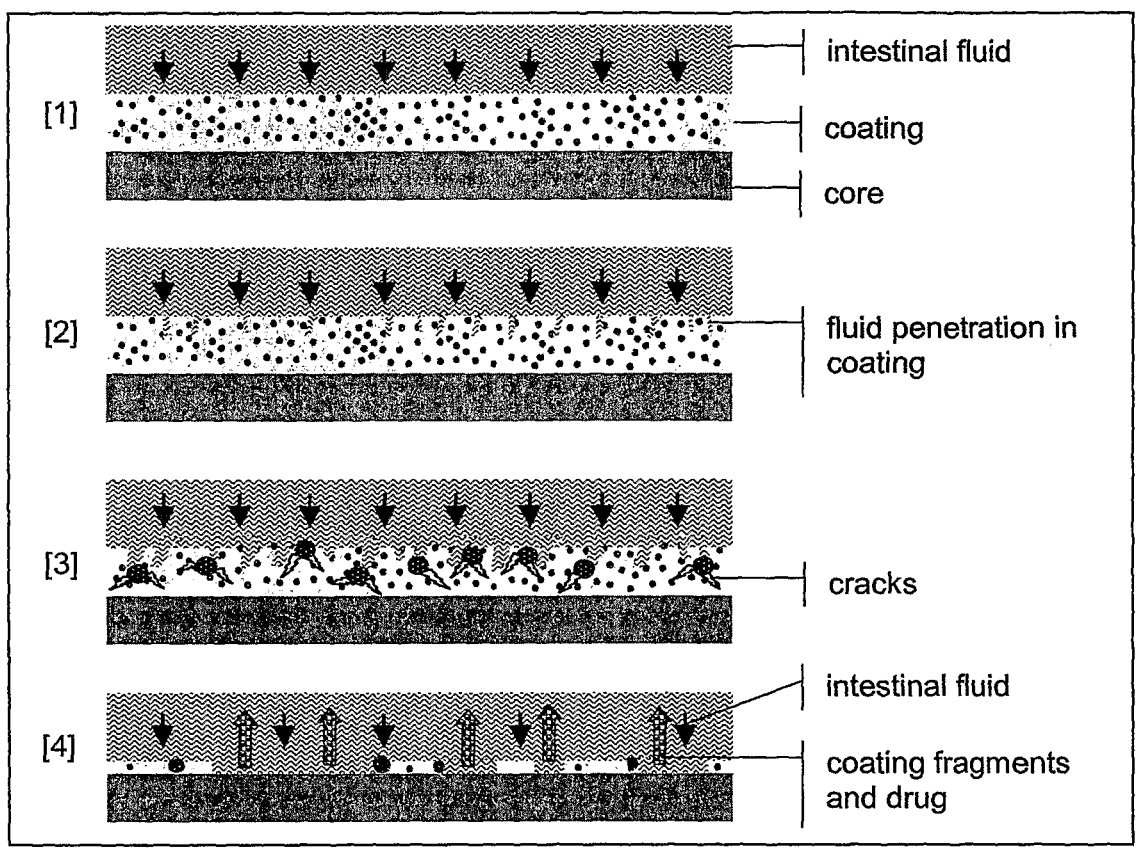

Sanchez et al., Rheological Properties of Food Gums as Related to their Water Binding Capacity and to Soy Protein Interaction, Lebensm. Wiss u.-Technol., 1995, pp. 380-385, vol. 28, Academic Press Limited.

Handbook of Pharmaceutical Excipients, Third Edition, 2000, entry for Sodium Starch Glycolate, pp. 501-504, American Pharmaceutical Association, Washington, DC.

Handbook of Pharmaceutical Excipients, Third Edition, 2000, Entry for Croscarmellose Sodium, pp. 160-162, American Pharmaceutical Association, Washington, DC.

Notice of Reasons for Rejection for copending 2015-214268 dated Aug. 24, 2016.

Leuenberger, Hans, The application of percolation theory in powder technology, Advanced Powder Technol., 1999, pp. 323-352, vol. 10, No. 4.

Leuenberger, Hans, New trends in the production of pharmaceutical granules: the classical batch concept and the problem of scale-up, European Journal of Pharmaceutics and Biopharmaceutics, Jun. 28, 2001, pp. 279-288, vol. 52.

Leuenberger et al., Percolation theory—a novel approach to solid dosage form design, International Journal of Pharmaceutics, Feb. 28, 1987, pp. 109-115, vol. 38.

Hastedt et al., Diffusion in Porous Materials Above the Percolation Threshold, Pharmaceutical Research, Mar. 1, 1990, pp. 893-901, vol. 7, No. 9.

Caraballo et al., Percolation theory: application to the study of the release behaviour from inert matrix systems, International Journal of Pharmaceutics, 1993, pp. 175-181, vol. 96.

Bonny et al., Matrix type controlled release systems, II. Percolation effects in non-swellable matrices, Pharmaceutica Acta Helvetiae, 1993, pp. 25-33, vol. 68.

Gareb et al. "Towards the Oral Treatment of Ileo-Colonic Inflammatory Bowel Disease with Infliximab Tablets: Development and Validation of the Production Process" Pharmaceutics 2019, 11, 428 (pp. 1-19).

Maurer et al. "Development and potential application of an oral ColoPulse infliximab tablet with colon specific release: A feasibility study" International Journal of Pharmaceutics 505 (2016) 175-186.

Stauffer et al., "Introduction to Percolation Theory," 2nd Edition, (1992), pp. 1-9.

Peppas et al "Hydrogels for oral delivery of therapeutic proteins" Expert Opin. Biol. Ther. (2004) 4(6):881-887.

Ritschel, WA, Angewante Biopharmazie, Stuttgart (1973), pp. 396-402.

Tarcha et al. "Polymers for Enteric Coating Applications in Polymers for Controlled Drug Delivery" CRC Press (1991) pp. 39-66.

\* cited by examiner

PH-CONTROLLED PULSATILE DELIVERY SYSTEM, METHODS FOR PREPARATION AND USE THEREOF

The invention relates to delivery systems that allows for the pulsatile release of a substance, such as a drug, in response to a change in pH. More specifically, it relates to drug administration to the gastrointestinal (GI) tract, in particular to site-specific intestinal drug delivery via the oral route. Provided is a pH-controlled release system that allows for a rapid release of a drug in response to the pH of intestinal fluids. The drug delivery system has the capability of complete loss of integrity in a very short period of time, allowing delivery of virtually all of the drug contained therein at the desired location/segment. This is achieved by surrounding the drug with a layer of pH sensitive coating material in which a swellable agent is embedded. The structure of the coating is such that the swellable agent is embedded in a continuous matrix of the pH sensitive coating polymer in a concentration below the percolation threshold. As soon as the outer layer of enteric coating material starts to erode upon a change in pH, GI fluid can reach the swellable agent, which swells enough to accelerate the further and complete disintegration of the coating and subsequently causes instant release of the drug at the target site.

Whereas the invention is illustrated by a pH-controlled drug delivery system, a skilled person will understand that the scope of the invention is not limited to the field of pharmaceutics or drug formulation. Rather, the invention finds its use in any situation wherein a rapid release of a substance in response to a change in pH is desirable. Examples of such fields are crop protection or detergents for washing.

Specific delivery of drugs to a selected location/segment in the GI tract is desired for the treatment of a wide variety of diseases and conditions. It is especially desirable to be able to deliver drugs so that they are targeted to specific regions of the GI tract. Targeting drugs to specific regions along the GI tract provides the ability to locally treat GI diseases, thus reducing side effects of drugs or inconvenient and painful direct delivery of drugs. Such specific delivery also potentially increases the efficiency of the drug and enables a reduction of the minimum effective dose of the drug. Furthermore, targeted delivery to certain parts in the GI tract may be advantageous when the absorption of a drug into the systemic circulation is limited to only a part of the GI tract. In such cases the absorption may be increased when the drug is delivered in a pulsatile and complete way within the GI absorption window, since it would increase the driving force for absorption at the site where it is specifically needed.

Significant variations in the pH occur in the GI tract with values ranging from approximately 1 in the stomach, 6.6 in the proximal small intestine and a peak of about 7.5 in the distal small intestine (Evans et al., 1988, Gut, 29:1035).

The pH differential between the stomach and small intestine has historically been exploited to orally deliver drugs to the intestinal tract by way of pH-sensitive polymeric coatings. Delivery of drugs to sites beyond the stomach is especially desirable for drugs that are destroyed by the acid conditions or enzymes of the stomach, or for drugs that cause adverse events by local activity in the stomach. The low stomach pH and presence of gastric enzymes have led to the development of oral drug dosage forms in which the drug is provided with an enteric coating.

Enteric coating materials exhibit resistance to acidic gastric fluids yet are readily soluble or permeable in intestinal fluid. Enteric polymeric materials are primarily weak acids containing acidic functional groups, which are capable of ionization at elevated pH. In the low pH of the stomach, the enteric polymers are protonized, and therefore, insoluble. As the pH increases in the intestinal tract, these functional groups ionize, and the polymer becomes soluble in the intestinal fluids. Thus, an enteric polymeric film coating allows the coated solid, e.g. a capsule comprising a drug, to pass intact through the stomach to the small intestine, where the drug is then released in a pH-controlled fashion. The drug can become available for absorption to the systemic circulation or locally in the GI-tract where it can exert its pharmacologic effects.

Enteric polymers currently used to coat oral pharmaceutical dosage forms include cellulose, vinyl, and acrylic derivatives. The most common enteric coatings are methacrylic acid copolymers (Eudragits), cellulose acetate phthalate, cellulose acetate succinate, and styrol maleic acid co-polymers (Ritschel, W. A., Angewante Biopharmazie, Stuttgart (1973), pp. 396-402; Agyilirah, G. A., et al., "Polymers for Enteric Coating Applications" in Polymers for Controlled Drug Delivery, Tarcha, P. J. ed., CRC Press, (1991) Boca Raton, pp. 39-66).

To obtain site specific delivery to certain parts in the gastro-intestinal tract several strategies exist. Time-response delivery systems are characterized by the fact that the drug is released after a certain period following the moment that the system has got in contact with water (swallowing of the system). However, the reliability of these systems is rather limited by the significant variations that occur in the oro-caecal transit time (OCTT). When the transit is faster or slower than expected the drug may be released at the wrong site or outside the absorption window of the drug. A second strategy exploits the differences that occur in environmental conditions at different sites in the GI-tract, thereby circumventing problems that may arise from variations in the OCTT. Two different sub-strategies exist; systems that respond to bacterial enzymes may be used to target the colon whereas systems that respond to pH variations may be used to target different sites in the g-i tract. The bacterial-enzyme dependent systems suffer from two major limitations in their performance. First of all the bacterial flora may vary from individual to individual, if the required bacteria are not present in a patient the drug may not be released at all. Furthermore, the release from these systems is in general very slow and pulsatile release is difficult to obtain. A pH-controlled drug delivery system has the advantage that it is site-specific. Just as bacterial-enzyme-dependent controlled formulations. It is largely independent of the orocaecal transit time (OCTT), which may vary between individuals. Furthermore, it is independent of the presence of bacteria. Finally, pH-sensitive polymers that allow for a site-specific release are readily commercially available.

However, an important limitation of this technique is the fact that the dissolution of the pH sensitive coating materials at pH values that are only slightly above their setpoint pH is rather slow. Since intestinal pH variations may lead to a situation in which the environmental pH is hardly above the setpoint pH at the target site, the dissolution/disintegration of the coating is often slow. As a consequence, the kinetics of drug release at the desired target location often displays a lag time of up to several hours or the drug will be released slowly over a period of several hours. Given the physiologically limited residence time at the target site, this lag time or low drug release severely limits the amount of drug that is effectively delivered at the target site. Furthermore, the GI motility pattern can vary widely in individual patients and in different disease states. In combination with the lag time or slow drug release, the site of drug release is hard to control. For instance, it may occur in an area ranging form ileum to deep in the colon.

Thus, it is an object of the present invention to provide a robust pulsatile delivery version of a pH-controlled delivery system. Pulsatile drug release triggered by a change in pH would allow for a rapid and site-specific release of a drug in the intestine. This provides an advantage where a high concentration of the drug is desirable for a relatively short period of time at a specific site in the intestinal tract, whether for therapeutic reasons or to effect a concentration-driven gradient to enhance absorption within the absorption window.

The present inventors surprisingly found that this goal is met if a disintegrating (e.g. swellable) agent is incorporated in the matrix of a pH-sensitive coating layer. As shown herein, this novel type of composite coating results in a significant increase in the rate of drug release when compared to conventional pH sensitive coating layers that do not contain a disintegrating agent. The invention therefore provides a pH-controlled pulsatile release system (PPRS) comprising a core surrounded by a coating layer, wherein said core comprises an active substance and wherein said coating layer comprises a pH-sensitive coating material wherein a swellable agent is embedded.

Without wishing to be bound by theory, it is thought that the swellable particles are embedded in a continuous matrix of the pH-sensitive polymer. An initial pH-dependent erosion of the composite coating layer due to dissolution of the pH-sensitive polymer, allows for the absorption of aqueous fluid by particles of swellable agent just beneath the surface of the coating layer. The outer shelf of the coating layer will be disrupted by the swelling of the swellable agent and the fluid can reach the underlying particles of swellable agent, as well as the still unwetted coating polymer. The coating layer will thus progressively be disrupted, resulting in complete and fast disintegration followed by a pulsatile release of the drug. The hypothetical drawings of FIG. 1 and the legend thereof provide further details about the proposed mechanism of pH-controlled pulsatile drug release according to the invention.

The term "swellable agent" or "swelling agent" as used herein refers to a compound or mixture of compounds capable of swelling upon absorption of an aqueous fluid. It is sometimes referred to in the area of drug formulation as 'disintegrating agent'. It is a hydrophilic material of natural, synthetic, or semi-synthetic origin. The swelling capacity of the swelling agent used for practicing the invention can vary. The swelling capacity is expressed as the amount of water the agent can absorb based on its own weight in a dry form. For example, an agent with a swelling capacity of 10 can absorb 10 times its weight in water. In one embodiment, the swellable agent has a swelling capacity of 1.1 or more, preferably 5 or more, more preferably 7 or more. Generally speaking, the higher the swelling capacity of the swellable agent in the composite enteric coating, the faster and more efficient the coating layer will disintegrate upon the initial pH-dependent erosion (dissolution) of the outer layer of the enteric coating material. Therefore, the swellable agent is preferably capable of taking up more than 7 times its weight in water, for instance at least 10 times, like 15 time or even more, like 20 or 25 times.

Suitable swelling agents for use in the present invention include sodium starch glycolate (Primojel™, Explotab™) or cross-linked carboxymethyl cellulose (Ac-Di-Sol™). However, the skilled person will understand that other types of swellable compounds, whether known or yet to be discovered, are also encompassed. Furthermore, a combination of two or more swellable agents may be used.

In one embodiment, sodium starch glycolate is used as swellable agent. Sodium starch glycolate is being used in oral pharmaceuticals as a disintegrant in capsule and tablet formulations. Disintegration occurs by rapid uptake of water followed by rapid and enormous swelling. However, its use in the matrix of a gastroresistant pH sensitive coating as provided herein is not described before. Sodium starch glycolate is the sodium salt of a carboxymethyl ether of starch. The molecular weight is typically 500 000-11 000 000. It is a very fine, white or off white, free flowing powder; odourless or almost odourless. It is practically insoluble in water and insoluble in most organic solvents. It consists of oval or spherical granules, 30-100 µm in diameter with some less-spherical granules ranging from 10-35 µm in diameter. In a preferred embodiment, Primojel® or Explotab™ is used as swelling agent. Primojel is a sodium starch glycolate USP-NF produced by cross-linking and carboxymethylation of potato starch and a subsequent purification. It complies with the latest editions of the Ph. Eur. (sodium starch glycolate type A, B and C), USP/NF (sodium starch glycolate type A and B), JPE. Both the degree of cross-linking and the degree of substitution were optimized in order to maintain maximum disintegration efficiency. Primojel® takes up 23 times its weight in water. The resulting high swelling capacity combined with high water penetration account for its high disintegration rate and efficiency.

The term "enteric coating material" as used herein refers to a pH-sensitive gastroresistant, coating material or mixtures thereof. Examples of suitable coating materials include cellulose acetate phthalate, hydroxypropyl methylcellulose phthalate, polyvinyl acetate phthalate and the EUDRAGIT™ acrylic polymers. Also included are advanced designs of swollen hydrogels prepared from neutral or intelligent polymeric networks (see Peppas et al., Expert Opin Biol Ther. 2004 June; 4(6):881-7 or WO 98/43615).

In a preferred embodiment, acrylic polymers are used. In one embodiment, Eudragit® L 100 or L 100-55 is used for drug delivery to the duodenum (pH>5.0). For delivery to the jejunum (pH>6.0), Eudragit® L 100 is suitably used. In another embodiment, the combination of Eudragit® S 100 and a swellable agent allows pulsatile drug release into the lower ileum and ascending part of the colon (pH 6.0 to 7.5). Site specific drug delivery can also be achieved by combining Eudragit® S 100 with Eudragit® L types.

The coating may also comprise one or more additives, for example a plasticizer which enhances film formation of the polymer and allows for the formation of a continuous, well cured and flexible coating layer. Suitable coating additives include polyethylene glycol (PEG), triethyl citrate (TEC), dibutyl sebacate (DBS), tributyl citrate, diethyl phthalate and acetyl tributyl citrate. In a specific aspect of the invention, the coating layer comprises an Eudragit, for example Eudragit S 100, in combination with a sodium starch glycolate as swellable agent and polyethylene glycol (PEG) as plasticizer. As demonstrated in the examples below, the release profile of a drug enclosed in a capsule coated with such a coating layer is pH-dependent and has a pulsatile character.

In another aspect, the invention provides a PPRS comprising a coating layer of Eudragit S 100 in combination with cross-linked carboxymethyl cellulose as a swellable agent. In a further aspect the invention comprises a coating layer of Eudragit L 100 in combination with sodium starch glycolate.

It should however be noted that the concept underlying the present invention, i.e. a composite coating layer comprising both a swellable agent and a coating material, is not restricted to a particular type of coating material. Thus, the invention is not limited to known pH sensitive coating materials but also encompasses yet to be discovered coating and/or swellable materials. Exact pH controlled drug release at a specific target site can be achieved by a combination of polymers.

The use of swelling agents to achieve a controlled drug release is known in the art. U.S. Pat. No. 4,871,549 discloses a time-controlled sustained-release drug delivery system in which drug release is caused by explosion of a membrane after a definite time period. The system comprises a preparation comprising a core, a drug, swelling agent and an outer membrane of water-insoluble coating material. When this system is placed into dissolution medium or the GI tract, water influx and the volume expansion of the swelling agent cause the explosion of the water permeable membrane. The drug thus releases after a predetermined time period. In contrast to the present invention, it is emphasized that the system of U.S. Pat. No. 4,871,549 is not influenced by the pH of the gastro-intestinal fluid. Furthermore, the swelling agent is present as a separate, internal layer and not incorporated in the external coating layer.

The OROS® push-pull system from Alza Company has been developed for pulsatile time-controlled delivery of water-soluble and water-insoluble drugs at a specific site (e.g., colon) in the GI tract. For example, the OROS-CT® system is based on the swelling properties of an osmotic core compartment which provides a pH-independent, time-controlled drug release.

European patent EP0384646 B1 describes a drug formulation that is contained within a water-insoluble capsule body and is sealed with a hydrogel plug. This drug delivery system is known under the name PULSINCAP™. Upon oral administration, the capsule cap dissolves in the gastric juice and the hydrogel plug swells. At a controlled and predetermined time point, the swollen plug is ejected from the PULSINCAP™ dosage form and the encapsulated drug is released.

European patent EP1021171 also relates to a time-controlled drug delivery system. It consists of a core comprising the drug and a swellable agent and a coating surrounding the core. The core consists of a water-insoluble, hydrophobic carrier wherein a water-insoluble hydrophilic particulate matter is incorporated. In the presence of an aqueous liquid, the particulate matter forms channels from the outer surface of the coating to the core. The channels control the rate of water entry into the core. The core material swells, bursts the coating and rapidly disintegrates to release the drug. There are a number of significant differences between EP1021171 and the present invention. First, the hydrophobic film and the hydrophilic particulate matter are insoluble in the fluids of the GI tract. Thus, in contrast to the invention the coating will remain insoluble irrespective of the pH. Second, the particulate matter is included in the carrier material to create channels through which water can enter the swellable core. The rate at which this time-controlled delivery system releases its enclosed drug depends on the thickness of the coating and the amount of particulate matter, i.e. the amount of channels. Thus, the amount of particulate matter in the coating is decisive for the moment of drug delivery, e.g. 4 or 6 hours following oral drug administration. The present invention however relates to a drug delivery system wherein the moment of drug release is determined by the pH of the local environment; the presence of the swellable agent does not influence the onset of drug release yet merely serves to speed up the process once it is triggered by a change in pH. Fourth, in EP1021171 a swellable core provides the force to ultimately break the surrounding coating. The system of the invention is clearly independent of the core. Fifth, EP1021171 requires the formation of a percolating matrix of the hydrophilic particulate matter within the hydrophobic carrier to ensure efficient channel formation. As will be described in more detail below, in a composite enteric coating of the invention the formation of a percolating matrix should be avoided, since this would lead to an immediate, pH-independent release of the drug. For a system of the invention it is crucial to use an amount of swellable agent below the percolation threshold.

WO 98/13029 discloses an Oral Delayed Immediate Release formulation comprising a compressed core containing one or more active substances surrounded with a coating containing one or more polymeric materials, wherein release of active substance(s) from the core is caused by rupture of the coating after a definite lag-time, said core comprising one or more immediate release carriers and having no substantial swelling properties upon exposure to GI fluids, and said polymeric coating materials being essentially non-soluble and/or non-erodable in GI fluids.

Thus, a pH-controlled pulsatile release system comprising a swellable agent embedded in a non-percolating manner in a matrix of pH-sensitive coating material as provided herein is not described before.

To ensure a pH-controlled release of the substance surrounded by the coating layer, the swellable agent should only become accessible to fluid upon an initial dissolution of the matrix in which it is embedded. Thus, the swellable agent must initially be shielded from fluids by the pH-sensitive coating material to prevent premature swelling and disintegration of the coating layer. It was found that this can be achieved when use is made of a suspension of particles of swellable agent in a solution of pH-sensitive coating material, such as enteric coating polymers or other pH-sensitive coating polymers. The coating suspension comprises a solvent or solvent mixture in which the coating material is soluble and in which the swellable agent is insoluble and non-swollen. Thus, the insoluble particles of swellable agent in the coating suspension are surrounded by coating material in a dissolved form. The coating suspension can be applied to the substance to be coated, e.g. by spraying. After removal of the solvent or solvent mixture, the resultant coating layer consists of a matrix of coating material in which particles of swellable agent are incorporated.

In a preferred embodiment, a coating suspension is prepared using an organic solvent. Most pH-sensitive coating materials are soluble in organic solvent, such as acetone or isopropyl alcohol, whereas useful swellable agents are insoluble in organic solvents and are in a non-swollen state in these solvents. In one aspect, a coating suspension comprises Eudragit as coating material and sodium starch glycolate as swellable agent in a mixture of an organic solvent and a small percentage of water, for example acetone:water [97:3, v/v]. The water serves as a plasticizer.

Since swellable particles that are located at the outer side of the coating layer may induce disintegration of the coating already before the desired pH setpoint is reached, the swellable agent containing coating may optionally be surrounded by a further thin coating layer comprising the pH-sensitive polymer without any swellable agents.

The performance of the coating is to a large extent dependent on the composition and structure of the coating material. An adequate performance is only obtained when a continuous film of pH-sensitive polymer exists and the swellable agent is embedded in a non-percolating way, so as to prevent the disintegration of the coating before the pH-setpoint is reached. The exact amount of swellable agent in a coating layer will depend on several factors, e.g. the physico-chemical properties of the coating material, the physico-chemical properties of the swellable agent (especially the particle size of the material is of high relevance here), the production process and the conditions during the process, further excipients that can be present in the coating and the like. A person skilled in the art will be able to experimentally determine the optimal amount of swellable agent for a particular situation without undue burden, for instance using a GI-simulation system described in Example 1. Based on the outcomes of initial experiments and general scientific knowledge on percolating systems, a person skilled in the art will be able to determine in what way the design and composition of a given formulation would have to change to obtain the desired performance. If for example the particle size of the swellable agent is decreased, its concentration in the coating layer should be decreased to prevent the formation of a percolating matrix of swellable material.

In another aspect, the invention provides a method for preparing a system for the pH-controlled pulsatile release of a solid substrate, comprising the steps of providing a coating suspension according to the invention, applying said suspension to a solid substrate and allowing evaporation of the solvent of the suspension such that a coating layer is formed wherein the swellable agent is embedded in a matrix of pH-sensitive coating material. The suspension is readily applied to the solid substrate using spray coating.

Furthermore, the use of a coating suspension described herein above is provided for the manufacture of a pulsatile pH-controlled release system, preferably a drug delivery system.

A pulsatile pH-controlled release system (PPRS) as provided herein allowing for the pulsatile release of a substance in response to a change in pH, comprising a core surrounded by a coating layer, wherein said core comprises the active substance. Also, mixtures of two or more active substances can be used. The coating layer can be applied directly onto the core such that the outer surface of the core is in contact with the inner surface of the coating layer. It is however also possible that one or more layer(s) are present which separate the outer surface of the core from the inner surface of the coating layer.

In a preferred embodiment, the active substance surrounded by a pH-sensitive coating layer is a drug, e.g. a drug for the treatment or prevention of disease. However, the active substance can also be a diagnostic substance, such as a traceable molecule e.g. a stable isotope. The core comprising the active substance is for example a capsule or tablet. The solid core comprising the substance and optionally additional materials can be covered with a coating suspension of the invention. The additional materials that can be employed in making drug-containing cores are any of those commonly used in pharmaceutics and should be selected on the basis of compatibility with the active drug and the physicochemical properties of the core. Included are binders, disintegrating agents, filling agents, surfactants, stabilizers and lubricants.

Suitable binders include cellulose derivatives such as methylcellulose, hydroxyethyl cellulose, hydroxypropyl cellulose, hydroxypropyl methylcellulose, polyvinylpyrrolidone, starches and the like.

Suitable swellable agents include corn starch, pregelatinized starch, cross-linked carboxymethylcellulose (AC-DI-SOL™), sodium starch glycolate (Primojel, EXPLOTAB™, cross-linked polyvinylpyrrolidone, alginic acid and any swellable agent known in the field of drug formulation. It was found that the incorporation of a swellable disintegration agent not only in the coating layer but also in the drug-containing core resulted in a pH-controlled drug delivery system with a highly pulsatile release profile.

Suitable filling agents include lactose, mannitol, microcrystalline cellulose calcium carbonate, calcium phosphate, calcium sulfate, microcrystalline cellulose, dextran, starches, sucrose, xylitol, lactitol, mannitol, sorbitol, sodium chloride, polyethylene glycol, and the like.

Examplary surfactants are sodium lauryl sulfate, sorbitan monooleate, polyoxyethylene sorbitan monooleate, bile salts, glyceryl monostearate, and the like.

Stabilizers such as any antioxidation agents, buffers, acids, and the like, can also be utilized.

Examples of lubricants are magnesium stearate, glyceryl behenate and sodium stearyl fumarate.

In one embodiment, the core comprising a drug is a drug-filled gelatin capsule, either with additional excipients, or alone. Typical excipients to be added to a capsule formulation include, but are not limited to: fillers such as microcrystalline cellulose, calcium phosphate dihydrate, calcium sulfate, lactose, sucrose, sorbitol, or any other inert filler. In addition, there can be flow aids such as fumed silicon dioxide, talc or any other material imparting flow to powders. A lubricant can further be added if necessary by using polyethylene glycol, leucine, glyceryl behenate, magnesium stearate or calcium stearate.

The drug may also be incorporated into a tablet or in pellets.

Specific embodiments of the present invention relate to a PPRS for the delivery of an active substance, e.g. drug or diagnostic molecule, to a specific site of the GI tract. Depending on the type of coating material used, said drug delivery system is for example a colon-specific drug delivery system or a duodenal-specific drug delivery system.

In a specific aspect, the invention provides a colon-specific PPRS, for example for the specific delivers of a drug, such as non-steroidal anti-inflammatory drugs (NSAIDs), cetrorelix or mesalasine (5-ASA), or a diagnostic molecule, such as carbohydrate stable isotopes, to the colon. The challenge of targeting drugs specifically to the colonic region of the GI tract is one that has been embraced by scientists over the past two decades. Previously thought of as a relatively innocuous organ, concerned solely with the adsorption of water and electrolytes and the formation and temporary storage of stool, the colon has recently become accepted as an increasingly important site in human physiology and for drug delivery. Research interest in the area of colonic drug delivery has been fuelled by the need to better treat pathologies of the colon that range in seriousness from constipation and diarrhoea to the debilitating inflammatory bowel diseases (ulcerative colitis and Crohn's disease) through to colon carcinoma, the third most prevalent form of cancer in both men and women. Targeted drug delivery to the colon would therefore ensure direct treatment at the disease site, lower dosing and a reduction in systemic side effects. Aside from local treatment, the colon can also be utilised as a port of entry for drugs into the bloodstream for the purpose of systemic therapy. For example, drugs (e.g. peptides or proteins) that are degraded and/or poorly absorbed in the upper part of the GI-tract may be preferentially absorbed from the colon because of the lower levels of digestive enzymes as compared with the small intestine. Furthermore, colonic drug delivery may also be used as means of achieving chromotherapy for diseases that are sensitive to circadian rhythms, such as asthma and arthritis.

Whereas the oral route is the preferred route of colonic drug administration in terms of convenience, this route is not without challenges. The colon constitutes the most distal segment of the GI tract and so an orally administered formulation must ideally retard (prevent) drug release in the upper GI regions but release the drug promptly on entry into the colon. Efficient protection of the drug to the diverse and hostile conditions of the stomach and small intestine can be achieved by the use of pH-sensitive coatings. However, the low fluid environment and viscous nature of luminal contents of the colon appear to hinder the dissolution and release of the drug from colon-specific formulations known thus far. The present inventors surprisingly observed that the latter problem could be solved by the incorporation of a swellable agent in the coating layer.

The inventors used a gastrointestinal simulation system (GISS; see Example 1) to investigate the kinetics of drug release of the model drug mesalazine (5-ASA) from capsules coated with pH-sensitive enteric coatings comprising different amounts of swellable agents. It was found (see Example 2) that the percentage swellable agent in the coating layer influences the onset and pulsatile nature of the release profile of a pH-controlled pulsatile release system of the invention. Drug release in phase IV of the GISS, simulating colon-specific release, was found to be around 90% of the total quantity released if 4 or 5% of the swellable agent Primojel was included in the coating suspension comprising Eudragit and PEG. A coating suspension comprising 10% Primojel resulted in a reduced colon-specificity with 56% drug release in phase IV. Thus, for this specific application of a PPRS according to the invention there appears to be an optimum range of the amount of swellable agent in the coating layer.

In a further embodiment, the invention provides a PPRS that specifically delivers a drug, for instance L-Dopa (also known as levodopa), to the duodenum. Oral administration of L-Dopa is currently a preferred way to treat the cerebral dopamine deficiency which causes Parkinson's disease. L-Dopa is optimally absorbed from the duodenum and proximal jejunum. The pharmacokinetic properties of L-Dopa lead to fluctuating blood levels, generating fluctuation of motor function in susceptible patients. Granules (containing L-Dopa) which are gastro-retentative based on buoyancy coated with a pH-sensitive pulsatile release coating as provided herein can be used to provide a continuous amount of drug in the absorption window, thereby preventing the fluctuating effects in motor function seen in current pharmacotherapy of Parkinson's disease.

In another embodiment, said site-specific delivery comprises the delivery of an active substance to specialized tissue of the small intestine. For example, the invention provides a PPRS for the delivery of an active substance, like a vaccine, to the Peyer's patches. Peyer's patches are a collection of large oval lymph tissues that are located in the mucus secreting lining of the small intestine. These lymph nodules are especially abundant in the lowest portion of the small intestine that empties into the larger intestinal tract, an area of the digestive system referred to as the ileum. They detect antigens and mobilizes highly specialized white blood cells termed B-cells to produce antibodies that are designed to attack foreign particles. Peyer's patches can be targeted by the application of a coating consisting of a polymer, such as Eudragit S100, combined with a swellable agent such as cross-linked carboxymethylcellulose (AC-DI-SOL™) and sodium starch glycolate (Primojel, EXPLOTAB™).

LEGENDS TO THE FIGURES

FIG. 1: Schematic drawing of the proposed mode of action of the swellable agent incorporated in a coating layer. In stage 1, the drug delivery system is exposed to intestinal fluid with a pH>7. The pH-sensitive polymer material in the coating layer starts to dissolve/erode. In stage 2, micro cracks or leakages are formed in the coating layer such that the particles of swellable agent that are present just beneath the surface become wetted. The fluid uptake by the swellable agent results in a dramatic increase of its volume (stage 3), accompanied by a further erosion of the coating layer, enhanced fluid penetration into the coating layer and swelling of the swellable agent. This cascade of events is responsible for a rapid and complete degradation of the coating layer such that the core surface, e.g. a drug capsule, becomes exposed to the environment (stage 4). There is a gradual transition of the initial pH-induced erosion to erosion that relies on exposure of swellable agent to aqueous fluid.

Figure 2:
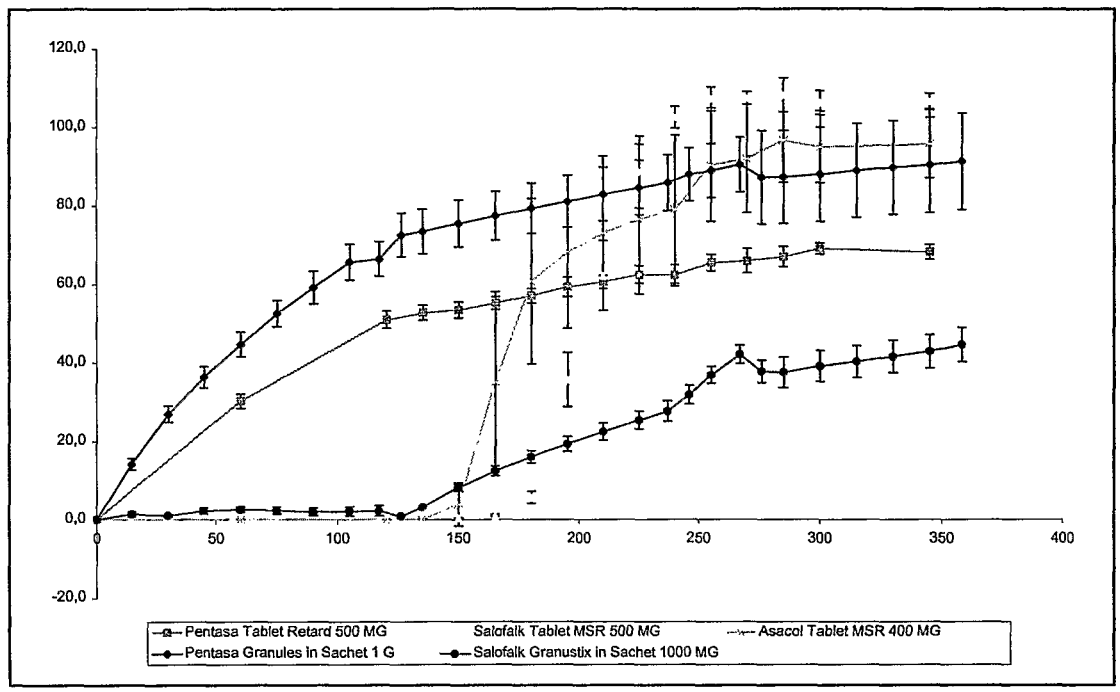

FIG. 2: Release profiles of various registered dosage forms of 5-ASA using the Gastro Intestinal Simulation System (GISS) described in Example 1. Phase I simulates the stomach, phase II the jejunum, phase III the distal ileum and phase IV the colon.

Figure 3:
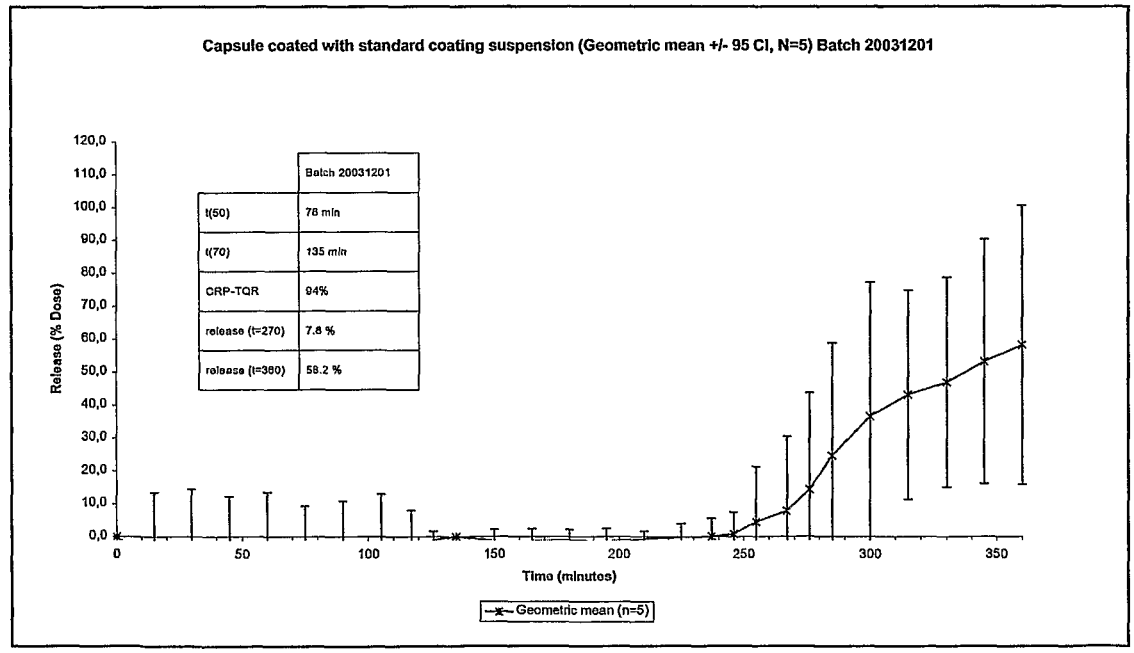

FIG. 3: Average release profile of 6 capsules containing 5-ASA provided with a coating of pH-sensitive polymer (Eudragit S100). Release of 5-ASA was determined over time using the GISS model described in Example 1. For further details see Example 2.

Figure 4:
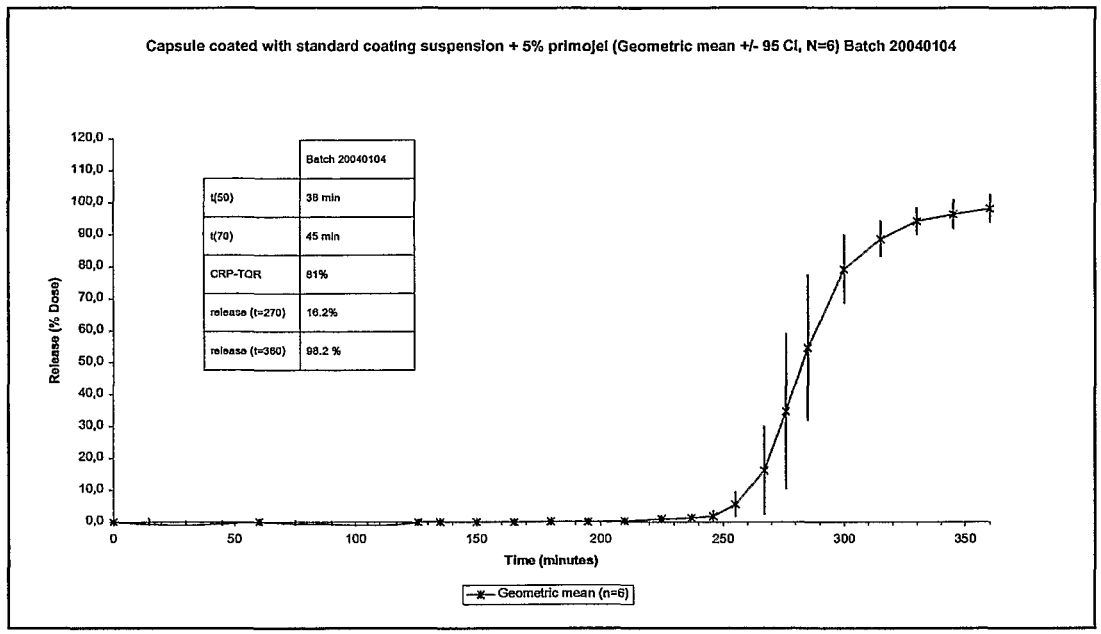

FIG. 4: Average release profile of 6 capsules containing 5-ASA provided with a coating of pH-sensitive polymer (Eudragit S100) and 5% swellable agent (Primojel®). Release of 5-ASA was determined over time using the GISS model described in Example 1. For further details see Example 2.

Figure 5:
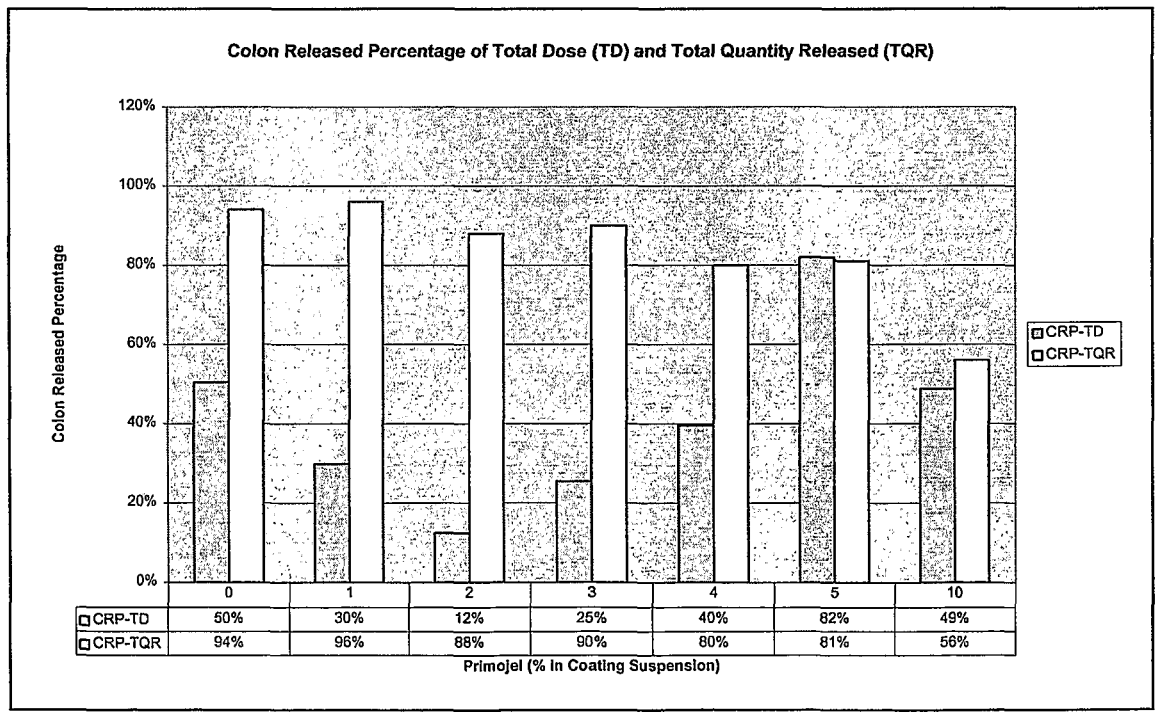

FIG. 5: Colon-selectivity of a Pulsatile pH-dependent Release System (PPRS) comprising a gelatine capsule with 50 mg of the drug 5-ASA, which capsule was provided with a coating layer (20 mg/capsule) of 7% Eudragit S100/1% PEG6000 and the indicated percentage of swellable agent (Primojel®). CRP-TQR refers to the Total Quantity Released, which is the percentage of 5-ASA released in phase IV, representing the colon, of the total actual release of 5-ASA in phases I through IV. The Colon Released Percentage of the Total Dose (CRP-TD) is the percentage of the total dose released in phase IV. For further details see Example 2.

Figure 6:
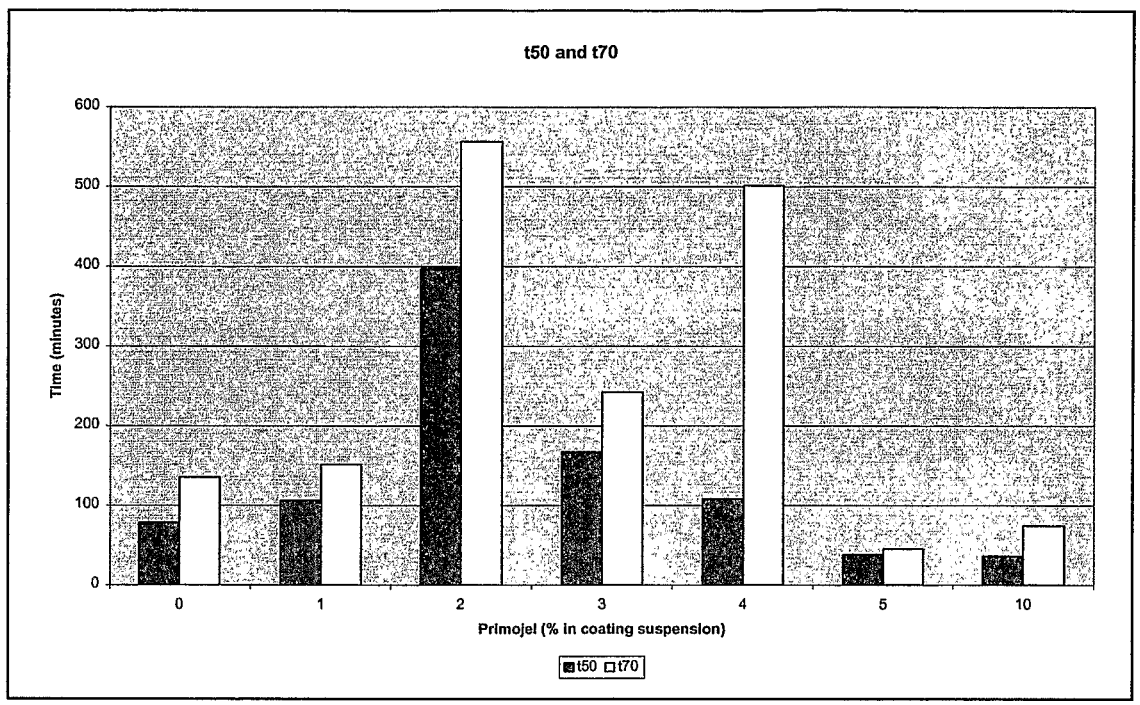

FIG. 6: Effect of the percentage of swellable agent in the coating suspension on the rate of pulsatile release of the drug. The rate is determined by measuring the time period required to release an average of 50% ($T_{50}$) or 70% ($T_{70}$) of the total drug dose relative to time zero ($T_0$) at which <5% drug release was detected.

EXAMPLES

The present invention will be further illustrated by way of the following Examples. These Examples are non-limiting and do not restrict the scope of the invention. A skilled person will understand that many different combinations of pH-sensitive coating materials and swellable agents are suitably used in a pH-controlled pulsatile release system of the invention, of which the specific formulations can be determined empirically.

Example 1

Gastro-Intestinal Simulation System (GISS)

This example describes the gastro-intestinal simulation system which was used by the present inventors to investigate the profiles of drug release of pH-controlled pulsatile drug delivery systems of the invention.

The drug mesalazine (5-ASA) was used as a test drug to evaluate and validate the GISS. 5-ASA is used in the therapy of ulcerative colitis and is readily absorbed in the proximal parts of the intestine. We tested the following commercially available oral dosage forms of 5-ASA: Salofalk® tablets, Salofalk® granules, Asacol® tablets, Pentasa® tablets and granules.

The GISS is a dissolution test which is based on the pharmacopoeial paddle method (apparatus II, Prolabo, Rhône-Poulenc, Paris, France) as described in the USP 26 and Ph. Eur. IV. During the test, a drug formulation is exposed to four phases simulating in subsequent order the stomach, the jejunum, distal ileum, and the proximal colon. Table 1 gives the specifications of these phases as well as the biorelevant media which were applied. The paddle was operated at 50 RPM and the system was kept at a temperature between 37±° C.

TABLE 1

Specifications of the four phases of the GISS

| Phase | GI-Segment | | Volume (mL) | Residence time (hour) | pH | Osmolality (mosmol/kg) |
|---|---|---|---|---|---|---|
| I | Stomach | Simulated Gastric Fluid sine pepsin (USP 26) | 500 | 2.0 | 1.2 ± 0.10 | 150 ± 25 |
| II | Jejunum | Simulated Intestinal Fluid sine pepsin (USP 24) + sodium chloride | 629 | 2.0 | 6.8 ± 0.10 | 250 ± 50 |
| III | Ileum (distal) | Simulated Intestinal Fluid sine pepsin (USP 23) + sodium chloride | 940 | 0.5 | 7.5 ± 0.10 | 250 ± 50 |
| IV | Colon (proximal) | Simulated Colonic Fluid | 1000 | 1.5 | 6.0 ± 0.10 | 250 ± 60 |

The buffering capacity was tested by measuring the pH in a GISS with and without 5-ASA. It was also tested whether the osmolality remains within specification during dissolution tests.

Release Measurements

The release profile of the modified oral dosage forms was determined by measuring the concentration of 5-ASA spectrophotometrically using an Ultraspec 4052 TDS apparatus (LKB, Zoetermeer, The Netherlands). The specific extinction of 5-ASA in each phase was determined (n=5) at λ=331 nm (Table 2.). If the concentration measured were out of the linear detection range, absorbance was measured off line after dilution of the sample with 3 N hydrochloric acid and subsequent measurement at λ=303 nm. The specific extinction of 5-ASA is then 236.0.

TABLE 2

Specific extinction of 5-ASA per phase

| Phase | Specific extinction at λ = 331 nm |
|---|---|
| I | 17.3 |
| II | 209.5 |
| III | 218.2 |
| IV | 161.4 |

Calculations

Release rates were calculated by dividing the amount released per phase by the residence time. Colon selectivity can be expressed by 3 different parameters. The Colon Released Percentage of the Total Quantity Released (CRP-TQR), which is the percentage released in phase IV of the total release in phase I until IV. Secondly, the Colon Released Percentage of the Total Dose (CRP-TD) is the percentage of the dose released in phase IV. Thirdly, the Colonic Selectivity Ration (CSR) is a dose-independent parameter indicative of the colon selective release of the dosage form relative to the other three release phases of the GISS. It is calculated by dividing the fraction released in phase IV by the cumulative fraction in the earlier three phases.

Results

Gastro-Intestinal Simulation System

An important aspect of in vitro dissolution testing of pH-controlled dosage forms is that there may only be a limited influence of the compound being released on the pH itself. In table 3 it is shown that the GISS has enough buffering capacity to keep the pH within the specified range (see Table 1) during the release of 5-ASA in the four phases. Furthermore, the osmolality remained within specification (Table 1), irrespective of the presence of 50 mg of 5-ASA.

TABLE 3

Average pH ± standard deviation measured in GISS

| | n | I | II | III | IV |
|---|---|---|---|---|---|
| Blank | 2 | 1.21 ± 0.01 | 6.85 ± 0.03 | 7.54 ± 0.01 | 6.29 ± 0.00 |
| 500 mg 5-ASA | 2 | 1.22 ± 0.00 | 6.67 ± 0.03 | 7.31 ± 0.05 | 6.10 ± 0.05 |
| Salofalk(r) Tablet MSR 500 MG | 6 | 1.16 ± 0.01 | 6.85 ± 0.02 | 7.52 ± 0.05 | n.m.[1] |
| Salofalk(r) Granustix in Sachet 1000 MG | 6 | 1.18 ± 0.01 | 6.86 ± 0.01 | 7.67 ± 0.01 | 5.89 ± 0.01 |

TABLE 3-continued

| Average pH ± standard deviation measured in GISS | | | | | |
|---|---|---|---|---|---|
| | n | I | II | III | IV |
| Asacol(r) Tablet MSR 400 MG | 5 | 1.12 ± 0.00 | 6.63 ± 0.06 | 7.25 ± 0.05 | 6.12 ± 0.06 |
| Pentasa(r) Tablet Retard 500 MG | 6 | 1.14 ± 0.02 | 6.65 ± 0.02 | 7.34 ± 0.03 | 5.97 ± 0.04 |
| Pentasa(r) Granules in Sachet 1 G | 6 | 1.23 ± N.A. | 6.79 ± N.A. | 7.54 ± N.A. | 5.77 ± N.A. |

[1]Not measured

3.2 Release Profiles

In FIG. 2, the release profiles of the tested products are shown. As would be expected, the products with a pH-sensitive coating (Salofalk® tablets, Salofalk® granules and Asacol® tablets) do not release any 5-ASA in the simulated stomach under fasted conditions (phase I). Furthermore, it is shown that Salofalk® tablets release 5-ASA more proximal than Asacol® tablets. Both do not release much 5-ASA in the simulated proximal colon. Pentasa® tablets as well as Pentasa® granules release a substantial amount (50-70%) of 5-ASA during a 2 hour stay in SGFsp (USP 26). Moreover, both Pentasa® tablets and Pentasa® granules release 5-ASA in the simulated stomach 3 to 5 times faster than in the simulated small and large intestine (Table 4.). Salofalk® granules show a lag time after which the release starts with zero-order kinetics. All products perform according to their pharmaceutical technological concepts.

TABLE 4

Release rates during the different phases for the tested products (standardised to a dose of 500 mg)

| | Release rate (mg/min per phase) | | | |
|---|---|---|---|---|
| | I | II | III | IV |
| Salofalk(r) Tablet MSR 500 MG | 0.0 | 4.3 | 0.8 | 0.0 |
| Salofalk(r) Granustix in Sachet 1000 MG | 0.1 | 1.2 | 2.5 | 0.4 |
| Asacol(r) Tablet MSR 400 MG | 0.0 | 3.3 | 2.2 | 0.2 |
| Pentasa(r) Tablet Retard 500 MG | 2.1 | 0.5 | 0.6 | 0.1 |
| Pentasa(r) Granules in Sachet 1 G | 2.8 | 0.6 | 0.6 | 0.2 |

In Table 5 the colon selectivity is given for each product. The data show that the actual colonic selectivity of the products is rather poor. Only the pellet products show a certain degree of colonic selectivity.

TABLE 5

CRP-TQR and CRP-TD for the tested products

| Product | CRP-TQR | CRP-TD |
|---|---|---|
| Salofalk Tablet MSR 500 MG | 0.0% | 0.0% |
| Pentasa Tablet Retard 500 MG | 3.3% | 2.2% |
| Asacol Tablet MSR 400 MG | 3.8% | 3.7% |
| Pentasa Granules in Sachet 1 G | 4.7% | 4.1% |
| Salofalk Granustix in Sachet 1000 MG | 14.8% | 6.8% |

Conclusions

The release profiles of all products are in agreement with their technological concepts and with available in vivo data. The percentage of the dose released in the simulated colon is small in all products. The GISS is a robust system able to discriminate between different types of modified-release oral dosage forms. It reveals release profiles with in vivo relevance and is thus suitably used for the evaluation of site-specific delivery systems of different substances.

Example 2

Development of a Pulsatile pH-Controlled Release System (PPRS)

This example demonstrates the beneficial effects of embedding a swellable agent (in this case sodium starch glycolate sold under the trade name Primojel) in a coating layer of pH-sensitive enteric coating material.

Materials and Methods

A standard coating solution was prepared comprising 7% poly-acrylate resin (Eudragit S100) and 1% PEG6000 in a solvent mixture of acetone/water [97:3; by volume]. The standard coating solution was supplemented with various amounts (1, 2, 3, 4, 5, or 10% (w/v) of Primojel to produce different coating suspensions. In a second experiment, capsules were coated with an improved coating procedure. The standard coating solution was supplemented with various amounts (4, 5, 6, 7% w/v) of Primojel.

The coating suspensions were applied by spray coating (Capsule Coater, Labo Tech) onto hard gelatine capsules in an amount of 20 grams coating suspension per 20 capsules. The capsules comprised 50 mg 5-ASA and Avicel™. The charge size was 20 capsules. Following the coating step, the capsules underwent a heat treatment of 1 hour at 50° C. to allow evaporation of the solvent mixture and curring of the polymeric film such that a composite coating layer was formed around the capsules.

Tests Performed

The GISS described in Example 1 was used to investigate the release profiles of 5-ASA from each batch of coated capsules. The average release profiles were determined on line by determining every 3 minutes the concentration of 5-ASA using spectrophotometry at 331 nm (n=6).

Calculations

The release rate is being expressed as the time needed tot release 50% ($t_{50}$) respectively 70% ($t_{70}$) of the content, calculated form the last measurement below 5%. The colon selectivity is being expressed by three parameters:

1. the colon released percentage of the total quantity released (CRP-TQR)
2. the colon released percentage of the total dose (CRP-TD)

Results

FIG. 3 shows the average geometric mean of the release profiles of five individual capsules that were coated the standard coating solution, i.e. without swellable agent. FIG. 4 shows the average release profiles of six individual capsules provided with 20 g of a coating layer comprising 5% swellable agent. Capsules coated without swellable agent exhibit insufficient release of 5-ASA (50.4%) after 360 min in the GISS. In addition, a large variation in the released dose is observed (5 to 98%). The addition of swellable agent to the coating suspension results in a pulsatile release profile, after a lag phase of around 240 minutes. Clearly, the presence of the swellable agent in the coating layer enhances the rate of drug release from the capsule, reduces the inter-capsule variation, enhances the CRP-TD. In Table 6 all data are shown.

TABLE 6

Characterization of capsules provided with a coating comprising varying concentrations of the swellable agent Primojel.

| % Primojel | t50 | t70 | Release (t = 270) | Release (t = 360) | CRP-TD | CRP-TQR |
|---|---|---|---|---|---|---|
| 0% | 78 min | 135 min | 7.8% | 58.2% | 50.4% | 94% |
| 1% | 106 min | 151 min | 1.5% | 31.4% | 29.9% | 96% |
| 2% | 397 min | 556 min | 1.7% | 14.1% | 12.4% | 88% |
| 3% | 167 min | 242 min | 3.6% | 29.0% | 25.4% | 90% |
| 4% | 108 min | 501 min | 9.2% | 48.8% | 39.6% | 80% |
| 5% | 38 min | 45 min | 16.2% | 98.2% | 82.0% | 81% |
| 10% | 36 min | 74 min | 28.8% | 77.6% | 48.8% | 56% |

The influence of the amount of swellable agent in the coating layer on the colon-selective drug release is graphically shown in FIG. 5. Colon selectivity is expressed in CRP-TQR and CRP-TD (see for abbreviations Example 1). Capsules coated with standard coating solution comprising 0-5% Primojel display a CRP-TQR of more than 80%. The CRP-TQR is lower in capsules coated with 10% Primojel in the coating suspension. Only at a concentration of 5% Primojel, a large fraction of the total drug dose is released in the simulated proximal part of the colon, as reflected by a high CRP-TD. An average of 82% of the total dose of 5-ASA is released in phase IV of the GISS, while the other capsules tested only released up to 50% in phase IV.

FIG. 6 demonstrates the effect of the percentage of Primojel in the coating suspension on the rate of pulsatile release of the drug. This rate is determined by measuring the time period required to release an average of 50% ($T_{50}$) or 70% ($T_{70}$) of the total drug dose relative to time zero ($T_0$) at which <5% drug release was detected.

Example 3

Optimalisation of the PPRS

This Example describes an optimalisation of the procedure described in Example 2 for the manufacture of a pulsatile pH-controlled release system. The optimalisation involved primarily mechanical aspects of the coating process, such as shortening of the inlet and outlet tubing, prerunning of the pump and the use of standardised glasswork and stirring bar for the supply of coating suspension. Furthermore, a swellable agent was included not only in the coating layer but also in the core.

Materials and Methods

Gelatine capsules filled with avicel, 50 mg 5-ASA and 5% Primojel were coated with a coating suspension comprising 7% Eudragit S100 and 1% PEG 6000 in a mixture of acetone/water [97:3]. The coating suspension furthermore contained 4, 5, 6 or 7% [m/v] Primojel. The capsules were coated with 20 grams of coating suspension as described in Example 2. Each batch comprising 20 capsules was tested in the GISS described in Example 1 to determine the release profile of 5-ASA.

Results

Colon-selective release was expressed as CRP-TQR and CRP-TD (see Example 1 for explanations of these abbreviations). As indicated in Table 7, drug release from capsules coated with 4 or 5% Primojel occurred for nearly 90% in phase IV of the GISS (CRP-TQR). The remainder was released in phase 3. Drug release in the simulated proximal part of the colon of the capsules coated with 4 or 5% Primojel was found to be 67% and 59% of the total dose, respectively (CRP-TD). Both parameters decreased with an increase of the percentage Primojel in the coating due to a shortened opening time of the coating. For capsules with 6 or 7% Primojel the onset of release occurred in the second phase of the GISS ($T_0$ was 155 and 149 minutes, respectively). The early erosion resulted in an early disruption of the coating during phase III. In contrast, the $T_0$ of the 4 and 5% capsules was 186 and 183 minutes, respectively.

TABLE 7 data of measurements of capsules coated according to the improved coating procedure as described in Example 3.

| % Primojel | $T_{50}$ | $T_{70}$ | Release (t = 270) | Release (t = 360) | CRP-TD | CRP-TQR |
|---|---|---|---|---|---|---|
| 4% | 40 min | 63 min | 6.4% | 87.4% | 81.0% | 89% |
| 5% | 54 min | 87 min | 8.3% | 78.3% | 70.0% | 89% |
| 6% | 30 min | 38 min | 31.0% | 87.6% | 56.6% | 58% |
| 7% | 28 min | 43 min | 30.6% | 87.8% | 57.2% | 50% |

All capsules tested displayed a pulsatile drug release profile, as is illustrated by the $T_{50}$ and $T_{70}$ values represented in Table 7. Capsules coated with 4% Primojel coating suspension released 70% of the drug within 67 minutes from the onset of drug release. An increase of the percentage of Primojel was accompanied by a decrease in the rate of drug release; the inclusion of 7% Primojel in the coating suspension yielded a $T_{70}$ of 99 minutes. In conclusion, although all percentages tested displayed a good pulsatile release profile, the concentration of 4 or 5% Primojel works best with regards to (simulated) colon-specific release.

Example 4

This Example describes the use of a second type of swellable agent. A standard coating solution was prepared comprising 7% poly-acrylate resin (Eudragit S100) and 1% PEG6000 in a solvent mixture of acetone/water [97:3; by volume]. The standard coating solution was supplemented with various amounts (0, 3 and 5%) of Ac-Di-Sol™ as swellable agent to produce different coating suspensions. The coating suspensions were applied by spraycoating (Capsule Coater, Labo Tech) onto gelatinised capsules in an amount of 50±5 mg dry coating material per capsule. The capsules comprised 50 mg 5-ASA, avicel and 5% Primojel™. The charge size was 20 capsules. Following the coating, the capsules underwent a heat treatment of 1 hour at 50° C. to allow evaporation of the solvent mixture and curring of the polymeric film such that a composite coating layer was formed around the capsules.

The capsules were tested in the GISS described in Example 1 to investigate the release profiles of 5-ASA from each batch of coated capsules.

Results:

Table 8 shows the results of the release measurements performed on the capsules containing different Ac-Di-Sol amounts. Given in the table are the total amount of drug released during the test (Released), the time at which the drug release started ($T_0$), the time needed to release 50% of the drug after the release was started ($T_{50}$), the time to release 70% of the drug ($T_{70}$) and the Colon Released Percentage of the Total Quantity Released (CRP-TQR).

TABLE 8

Results of the drug release studies with Eudragit S100 coatings containing different amounts of Ac-Di-Sol

|  | Released (%) | $T_0$ (min) | $T_{50}$ (min) | $T_{70}$ (min) | CRP-TQR |
|---|---|---|---|---|---|
| Ac-Di-Sol 0% | 19 | 255 | >105 | >105 | — |
| Ac-Di-Sol 3% | 94 | 246 | 18 | 27 | 36 |
| Ac-di-Sol 5% | 87 | 243 | 17 | 28 | 26 |

The results clearly show that inclusion of the Ac-Di-Sol to the coating increases the pulsatile character of the drug release and increases the amount of drug delivered to the colon.

Example 5

In another embodiment an aqueous dispersion of the following composition was made:

| Water | 22.71 g |
|---|---|
| Eudragit S100 | 8.43 g |
| Ammonia (1 M) | 4.29 g |
| Triethyl Citrate | 4.22 g |
| Primojel ™ | 0.12 g |

The dispersion rapidly turned into a highly viscous mass which could not be sprayed onto tablets, capsules or pellets. This indicates that the use of an aqueous solvent is not suitable for the production of the system described in this application.

The invention claimed is:

1. A release system comprising:
a core comprising an active substance, and,
surrounding the core, a coating layer comprising a swellable agent embedded in pH-sensitive coating material,
wherein the swellable agent is embedded in a continuous matrix of the pH-sensitive coating material at a concentration below the percolation threshold of the swellable agent in the continuous matrix of the pH-sensitive coating material,
wherein the swellable agent, in its dry form, is able to take up at least five times its weight in water; and
wherein the embedded swellable agent is dispersed within the pH-sensitive coating material in the coating layer and is shielded from fluids by the pH-sensitive coating material.

2. The release system according to claim 1, wherein said swellable agent is selected from the group consisting of sodium starch glycolate and cross-linked carboxymethylcellulose sodium.

3. The release system of claim 1, wherein said pH-sensitive coating material is selected from the group consisting of cellulose acetate trimellitate, hydroxypropyl methylcellulose phthalate, polyvinyl acetate phthalate, and co-polymerized methacrylic acid/methacrylic acid methyl esters.

4. The release system of claim 1, wherein said coating layer further comprises an additive.

5. The release system according to claim 1, wherein said active substance is selected from the group consisting of neurotransmitters, L-DOPA, hormone agonists, hormone antagonists, cetrorelix, steroidal or non-steroidal anti-inflammatory drugs, stable isotopes, an immunogenic substance, a vaccine and a combination of any thereof.

6. A method for preparing the release system of claim 1, comprising the steps of:
providing a coating solution comprising a mixture of a pH-sensitive coating material and a swellable agent in a solvent or solvent mixture, wherein said coating material is soluble in said solvent and wherein said swellable agent is insoluble and non-swollen in said solvent,
applying said coating solution to a solid substrate, and
evaporating the solvent of the coating solution resulting in a coating layer where the swellable agent is embedded in a matrix of pH-sensitive coating material.

7. A pharmaceutical composition comprising:
the release system of claim 1, and
a pharmaceutically acceptable carrier.

8. A method for site specific delivery of a drug, the method comprising:
administering to a subject in need thereof a suitable amount of the pharmaceutical composition according to claim 7.

9. The release system of claim 1 wherein the core comprises a pharmaceutically active substance.

10. The release system of claim 1, wherein the swellable agent is able to take up at least 10 times its weight in water.

11. The release system of claim 4, wherein the additive is a plasticizer selected from the group consisting of polyethylene glycol (PEG), triethyl citrate (TEC), and tributyl sebacate (TBS).

12. The method according to claim 6, wherein the solvent or solvent mixture comprises organic solvent, acetone, or isopropyl alcohol.

13. The method according to claim 6, wherein applying the coating suspension to a solid substrate comprises spray coating.

14. The release system of claim 1, wherein the release system is a system selected from the group consisting of a drug delivery system, a colon specific drug delivery system, and a duodenal specific drug delivery system.

15. The method according to claim 8, wherein the site specific drug delivery comprises colon specific and/or duodenal specific drug delivery.

16. A release system, wherein the release system is selected from the group consisting of a drug delivery system, a colon specific active substance delivery system, and a duodenal specific active substance delivery system, said release system comprising:
a core comprising a pharmaceutically active substance, and
a coating layer surrounding said core, said coating layer comprising:
a pH-sensitive coating material selected from the group consisting of cellulose acetate trimellitate, hydroxypropyl methylcellulose phthalate, polyvinyl acetate phthalate, and co-polymerized methacrylic acid/methacrylic acid methyl esters, and
a swellable agent selected from the group consisting of sodium starch glycolate and cross-linked carboxymethylcellulose sodium,
wherein particles of the swellable agent are embedded in a non-percolating way in a continuous matrix of the pH-sensitive coating material at a concentration below the percolation threshold of the swellable agent in the continuous matrix of the pH-sensitive coating material,
wherein the swellable agent, in its dry form, is able to take up at least 5 times its weight in water, and wherein the particles of swellable agent are dispersed within the pH-sensitive coating material in the coating layer and are shielded from fluids by pH-sensitive coating material.

17. The method according to claim 6, wherein the coating solution comprises 4% of the swellable agent.

18. The method according to claim 6, wherein the coating solution comprises 5% of the swellable agent.

19. The method according to claim 6, wherein the coating solution comprises 6% of the swellable agent.

20. The method according to claim 6, wherein the coating solution comprises 7% of the swellable agent.

* * * * *